United States Patent
Robertson (10) Patent No.: US 10,560,620 B2
(45) Date of Patent: Feb. 11, 2020

(54) IMAGE ACQUISITION APPARATUS (71) Applicant: EPIPOLE LIMITED, Rosyth, Fife (GB)

(72) Inventor: Craig Robertson, Aberdour (GB)

(73) Assignee: EPIPOLE LIMITED, Rosyth (GB)

( * ) Notice: Subject to any disclaimer, the term of this patent is extended or adjusted under 35 U.S.C. 154(b) by 381 days.

(21) Appl. No.: 14/434,756

(22) PCT Filed: Oct. 24, 2013

(86) PCT No.: PCT/GB2013/052783
§ 371 (c)(1),
(2) Date: Apr. 9, 2015

(87) PCT Pub. No.: WO2014/064454
PCT Pub. Date: May 1, 2014

(65) Prior Publication Data
US 2015/0296109 A1 Oct. 15, 2015

(30) Foreign Application Priority Data
Oct. 25, 2012 (GB) .................................... 1219171.4

(51) Int. Cl.
*H04N 5/225* (2006.01)
*G06T 1/00* (2006.01)
*G06T 7/00* (2017.01)

(52) U.S. Cl.
CPC ......... *H04N 5/2256* (2013.01); *G06T 1/0007* (2013.01); *G06T 7/0012* (2013.01); *G06T 2207/30041* (2013.01)

(58) Field of Classification Search
CPC ......... H01L 2924/0002; H01L 51/5253; H01L 51/5056; H01L 51/56; H01L 27/3244;
(Continued)

(56) References Cited

U.S. PATENT DOCUMENTS 6,032,071 A * 2/2000 Binder ................. A61B 5/0059
356/369
6,106,457 A 8/2000 Perkins et al.
(Continued)

FOREIGN PATENT DOCUMENTS

DE 251097 11/1987
EP 1058860 10/2003
(Continued)

*Primary Examiner* — Dave Czekaj
*Assistant Examiner* — Kehinde Abimbola
(74) *Attorney, Agent, or Firm* — Liu & Liu (57) ABSTRACT

The present invention relates to portable image acquisition apparatus (10). The portable image acquisition apparatus (10) is configured to acquire at least one image of apart of a human or animal body. The portable image acquisition apparatus comprises a main body (12) defining a window (20) and an imaging arrangement (16) operable to acquire an image of a part of a human or animal body by way of an imaging path which passes through the window (20). The portable image acquisition apparatus (10) also comprises a lighting module (14) comprising a light source and an optical arrangement (50), the lighting module (14) and the main body (12) being configured to releasably couple with each other when in use. The light source is configured to emit a beam of non-coherent light in a direction substantially perpendicular to the imaging path. The optical arrangement (50) is configured to receive the beam of light and change a direction of propagation of the received light whereby a beam of light is directed through the window (20). The portable image acquisition apparatus (10) is configured such that between the optical arrangement (50) and the window the imaging path and the beam of light have substantially opposite directions and at least in part occupy the same space.

23 Claims, 5 Drawing Sheets (58) Field of Classification Search
CPC ............ H01L 2924/00; H01L 51/5012; H01L 27/3246; H01L 27/3258; H01L 51/5016; G06T 19/006; G06T 11/60; G06T 15/04; G06T 19/003; G06T 19/20; G06T 2215/16; G06T 2219/024; G06T 2219/2016; G06T 2219/2021; G06T 7/0051; G06T 11/001; G06T 15/205; G06T 2200/04; H04N 7/183; H04N 5/2256; H04N 5/23293; H04N 5/23203; H04N 5/2354; H04N 5/247; H04N 5/332; H04N 7/181; H04N 5/2252; G06K 9/6202; G06K 9/209; G06K 9/00362; G06K 9/0002; G06K 9/00288; G06K 9/00342; G06K 9/00624; G06K 9/00771; G06K 2209/09; G06K 2209/21; G06K 9/00335; G06K 9/00369

See application file for complete search history.

(56) References Cited

U.S. PATENT DOCUMENTS

| | | | | |
|---|---|---|---|---|
| 6,314,248 | B1 * | 11/2001 | Ohmura | G02B 27/017 396/429 |
| 6,347,163 | B2 * | 2/2002 | Roustaei | G03F 7/705 235/462.21 |
| 6,385,352 | B1 * | 5/2002 | Roustaei | G03F 7/705 235/462.21 |
| 7,364,297 | B2 * | 4/2008 | Goldfain | A61B 3/158 351/205 |
| 7,385,625 | B2 * | 6/2008 | Ohmura | G02B 27/017 348/51 |
| 7,548,234 | B2 * | 6/2009 | Kawata | G09G 3/3648 345/204 |
| 7,622,164 | B2 * | 11/2009 | Jones | G02B 5/045 252/299.01 |
| 2001/0055422 | A1 * | 12/2001 | Roustaei | G03F 7/705 382/181 |
| 2002/0001472 | A1 * | 1/2002 | Ohmura | G02B 27/017 396/429 |
| 2002/0075481 | A1 * | 6/2002 | Roustaei | G03F 7/705 356/388 |
| 2003/0025876 | A1 | 2/2003 | Nanjo | |
| 2004/0085476 | A1 | 5/2004 | Whalen | |
| 2004/0130645 | A1 * | 7/2004 | Ohmura | G02B 27/017 348/333.08 |
| 2005/0110949 | A1 * | 5/2005 | Goldfain | A61B 3/158 351/206 |
| 2006/0142746 | A1 * | 6/2006 | Friedman | A61B 18/20 606/11 |
| 2006/0187171 | A1 * | 8/2006 | Kawata | G09G 3/3648 345/98 |
| 2006/0210726 | A1 * | 9/2006 | Jones | G02B 5/045 428/1.1 |
| 2007/0188855 | A1 * | 8/2007 | Shishkov | A61B 5/0062 359/362 |
| 2007/0299331 | A1 * | 12/2007 | Friedman | A61B 18/20 600/407 |
| 2009/0096914 | A1 * | 4/2009 | Domenicali | G01J 3/2803 348/345 |
| 2009/0246417 | A1 * | 10/2009 | Jones | G02B 5/045 428/1.31 |
| 2009/0316038 | A1 | 12/2009 | Schmack et al. | |
| 2010/0149743 | A1 * | 6/2010 | Shen | G06F 1/1616 361/679.21 |
| 2010/0155581 | A1 * | 6/2010 | Cho | G03G 15/0435 250/225 |
| 2010/0253885 | A1 * | 10/2010 | Jones | G02B 5/045 349/96 |
| 2011/0102550 | A1 * | 5/2011 | Daniel | G06T 7/55 348/46 |
| 2012/0147327 | A1 | 6/2012 | Shikaumi et al. | |
| 2012/0229617 | A1 | 9/2012 | Yates et al. | |
| 2012/0274815 | A1 * | 11/2012 | Matsumoto | H04N 5/232 348/240.99 |
| 2013/0010304 | A1 * | 1/2013 | Hsu | G01B 9/02028 356/496 |
| 2013/0033593 | A1 * | 2/2013 | Chinnock | A61B 3/0091 348/78 |
| 2014/0155757 | A1 * | 6/2014 | Yang | A61B 1/00108 600/476 |
| 2015/0002853 | A1 * | 1/2015 | Hsu | G01B 9/02028 356/497 |
| 2015/0015746 | A1 * | 1/2015 | Matsumoto | H04N 5/232 348/240.99 |
| 2017/0160132 | A1 * | 6/2017 | Shishkov | A61B 5/0062 |
| 2018/0010965 | A1 * | 1/2018 | Shishkov | A61B 5/0062 |

FOREIGN PATENT DOCUMENTS

| | | |
|---|---|---|
| WO | 96/36294 | 11/1996 |
| WO | 01/95791 | 12/2001 |
| WO | 2010/129775 | 11/2010 |
| WO | 2010/131944 | 11/2010 |
| WO | 2011/029064 | 3/2011 |
| WO | 2011/047214 | 4/2011 |

* cited by examiner

IMAGE ACQUISITION APPARATUS

FIELD OF THE INVENTION

The present invention relates to image acquisition apparatus which is configured for medical use and in particular but not exclusively apparatus configured to acquire at least one image of a part of a human or animal body. The present invention also relates to a method of acquiring at least one image of a part of a human or animal body.

BACKGROUND TO THE INVENTION

It is known to use electronic camera based technology for medical screening programmes, medical diagnosis and monitoring disease progression. For example apparatus comprising a retina camera and image acquisition circuitry is used in fundus photography by medical clinicians to acquire images of the interior surface of the eye. The acquired images are normally analysed later by a specialist to detect and evaluate symptoms of eye disease such as glaucoma.

In the developing world clinicians are making increasing use of telemedicine on account of the remoteness of the locations in which they practice and the need to move from location to location during the course of their work. The capability of known electronic camera based technology to provide transmissible images makes such technology appropriate for telemedicine applications. However electronic camera based medical apparatus and in particular apparatus for fundus photography is generally large and heavy and therefore unsuited to other than static operation. Such electronic camera based medical apparatus is normally difficult to move from location to location on account of its size and weight and is often not readily brought into operation after movement.

The present invention has been devised in the light of an appreciation of the above mentioned problems. It is therefore an object for the present invention to provide portable image acquisition apparatus which is configured for medical use and more particularly which is configured to acquire at least one image of a part of a human or animal body. It is a further object for the present invention to provide an improved method of acquiring at least one image of a part of a human or animal body.

Statement of Invention

According to a first aspect of the present invention there is provided portable image acquisition apparatus configured to acquire at least one image of a part of a human or animal body, the apparatus comprising:

a main body defining a window;
an imaging arrangement operable to acquire an image of a part of a human or animal body by way of an imaging path which passes through the window;
a lighting module comprising a light source and an optical arrangement, the lighting module and the main body being configured to releasably couple with each other when in use; and
the light source being configured to emit a beam of non-coherent light in a direction substantially perpendicular to the imaging path, and
the optical arrangement being configured to receive the beam of light from the light source and change a direction of propagation of the received light whereby a beam of light is directed through the window, the portable image acquisition apparatus being configured such that between the optical arrangement and the window the imaging path and the beam of light have substantially opposite directions and at least in part occupy the same space.

The portable image acquisition apparatus is brought into use by coupling the main body and the lighting module with each other. The portable image acquisition apparatus is disposed relative a part of a human or animal body such that an image of the part of the human or animal body can be acquired through the window. The imaging arrangement is operative to acquire an image of the part of the human or animal body by way of an imaging path which passes through the window. The portable image acquisition apparatus may be configured such that the imaging path between the window and the imaging arrangement is substantially straight. The lighting module comprises a light source and an optical arrangement. The light source is operative to emit a beam of non-coherent light in a direction substantially perpendicular to the imaging path. The optical arrangement is configured to receive the beam of light from the light source and to change a direction of propagation of the received light whereby a beam of light is directed through the window. In use, the beam of light that is directed through the window impinges upon the part of the human or animal body.

The portable image acquisition apparatus is configured such that between the optical arrangement and the window the imaging path and the beam of light have substantially opposite directions and at least in part occupy the same space. Configuring the portable image acquisition apparatus such that the imaging path and the beam of light have substantially opposite directions and at least in part occupy the same space between the optical arrangement and the window may obviate the need for pupil dilation, e.g. by way of eye drops, where the part of the human or animal body is an eye. The portable image acquisition apparatus may be configured such that the imaging path and the beam of light are substantially coaxial between the optical arrangement and the window. As described further below an acquired image may then be conveyed to a remote location for analysis. After use the lighting module may be released and thereby separated from the main body. Releasability of the lighting module from the main body may be advantageous when a lighting module requires repair or replacement. Alternatively one of plural lighting modules may be releasably coupled with the main body when it is desired to configure the portable image acquisition apparatus in a particular fashion. For example, a first lighting module may be configured to emit a beam of visible light and a second lighting module may be configured to emit a beam of infrared light with one of the first and second modules being brought into use depending on the form of image analysis to be performed.

The beam of light emitted by the light source may be narrowband. The beam of light may comprise light having a wavelength between 10 nm and 1 mm, 100 nm and 900 nm, 200 nm and 800 nm, 400 nm and 700 nm, 425 nm and 675 nm, 450 nm and 650 nm, 475 nm and 650 nm, 500 nm and 625 nm, or 525 nm and 600 nm.

The imaging arrangement may be constituted as a module. The imaging arrangement may therefore be separable from the main body. The main body and the imaging arrangement may be configured to releasably couple with each other when in use. After use the imaging arrangement may be released and thereby separated from the main body. Releasability of the imaging arrangement from the main body may be advantageous when an imaging arrangement requires repair or replacement. Alternatively one of plural imaging arrangements may be releasably coupled with the main body when it is desired to configure the portable image acquisition apparatus in a particular fashion. For example a first imaging arrangement may be optimised to acquire a broad spectrum image and a second imaging arrangement may be optimised to acquire a narrow spectrum image.

The portable image acquisition apparatus may be configured such that the lighting module and the imaging arrangement are coupled independently of each other to the main body. The lighting module may therefore be optically aligned with the main body independently of the imaging arrangement and vice-versa. The main body may define a first profile which is configured to engage with the lighting module. Alternatively or in addition the main body may define a second profile which is configured to engage with the imaging arrangement. The first and second profiles may be spaced apart from each other.

The light source may be configured to emit at least one of: visible light such as green light; infrared light; and ultra violet light. The light source may comprise at least one Light Emitting Diode (LED). The light source may be configured to emit light of a wavelength of greater than 10 nm, 380 nm, 450 nm, 520 nm, 620 nm, 700 nm or 750 nm. The light source may be configured to emit light of a wavelength of no greater than 1 mm, 750 nm, 700 nm, 620 nm, 520 nm, 450 nm or 380 nm. The light source may be configured to emit light of a wavelength of greater than 525 nm, 545 nm, 565 nm, 575 nm, 580 nm, 585 nm, 590 nm, 595 nm or 600 nm. The light source may be configured to emit light of a wavelength of no greater than 605 nm, 600 nm, 595 nm, 590 nm, 585 nm, 580 nm, 575 nm, 570 nm, 565 nm or 545 nm. The pupil normally exhibits peak sensitivity to light of a wavelength of 555 nm. The present inventor has appreciated that although light of a wavelength of 570 nm provides for good imaging of vasculature of the eye, the pupil still contracts readily at this wavelength and thereby reduces the effectiveness of the imaging. As the wavelength increases above 570 nm pupil contraction reduces further with there being hardly any contraction at 620 nm. A wavelength of around 590 nm has been found to provide an effective compromise between good imaging of oxygenated and deoxygenated blood, sensitivity of the imaging apparatus and pupil contraction sensitivity. The imaging apparatus may be configured to be responsive over a bandwidth corresponding generally and perhaps substantially to a bandwidth of light emitted by the light source. The imaging apparatus may be configured to be responsive at a wavelength of greater than 525 nm, 545 nm, 565 nm, 575 nm, 580 nm, 585 nm, 590 nm, 595 nm or 600 nm. The imaging apparatus may be configured to be responsive at a wavelength of no greater than 605 nm, 600 nm, 595 nm, 590 nm, 585 nm, 580 nm, 575 nm, 570 nm, 565 nm or 545 nm.

The light source may be configured to emit light of an intensity of no more than 20 candelas, 10 candelas, 5 candelas, 2 candelas or 1 candela. In a form the light source may be configured to emit light of an intensity of about 2 candelas.

As specified above the portable image acquisition apparatus is configured such that upon leaving the light source, the beam of light travels in a substantially perpendicular direction to the imaging path. The optical arrangement is configured to receive the beam of light and change a direction of propagation of the received light whereby a beam of light is directed through the window. The portable image acquisition apparatus is otherwise configured such that between the optical arrangement and the window the imaging path and the beam of light have substantially opposite directions and at least in part occupy the same space. One of the imaging path and the beam of light may be contained in the space occupied by the other of the imaging path and the beam of light. In a form of the invention, the imaging path and the beam of light may be substantially coextensive. The optical arrangement may be disposed in the imaging path. The optical arrangement may therefore be configured to allow for transmission of the image with substantially no change in a direction of the imaging path and for redirection of the beam of light.

The optical arrangement may be operative as a beam splitter. The optical arrangement may thus be disposed so as to reflect a proportion of light incident from the light source towards the window and to transmit a remaining proportion of the incident light, the reflected light being directed in an opposite direction to the imaging path. The optical arrangement may therefore comprise a beam redirection arrangement. In addition the portable image acquisition apparatus may be configured such that the image is incident on the beam redirection arrangement. The beam redirection arrangement may therefore be operative to transmit at least a part of the image, e.g. towards the imaging arrangement source. The beam redirection arrangement may also be operative to reflect at least a part of the image, e.g. towards the light source, with such reflection being termed image reflex. Transmission of light by the beam redirection arrangement may be subject to light loss in accordance with the normal operation of beam splitters such as in respect of light absorption.

In a first embodiment the beam redirection arrangement may comprise a beam splitter. The beam splitter may comprise a surface, such as forms part of a mirror, which at any location is partially reflective and partially transmissive, or a dichroic device. The present inventor found that a beam redirection arrangement according to the first embodiment provided for very little of light emitted by the light source being received at the imaging arrangement. In addition the beam splitter provided an undesirably large image reflex. The present inventor therefore conceived of a second embodiment of beam redirection arrangement.

In a second embodiment the beam redirection arrangement may comprise a substantially completely reflective surface and may define an aperture which provides for substantially complete transmission of light from the light source which impinges on the aperture. Light not impinging on the aperture, i.e. light impinging on the reflective surface, may be reflected towards the window. The aperture may be surrounded by the reflective surface. More specifically the aperture may be disposed towards a centre of the reflective surface. Light from the light source which falls on the reflective surface may therefore be substantially reflected towards the window and light from the light source which enters the aperture may be substantially transmitted. In addition the aperture may be disposed in the beam redirection arrangement so as to leave the imaging path substantially unimpeded whereby the image passes substantially through the aperture towards the imaging arrangement. In view of the reflective surface being disposed at an angle to the light source whereby light is redirected towards the window, opposing sides of the aperture may diverge away from each other to thereby minimise reflection of light received from the light source from the opposing sides and allow for passage of the image towards the imaging arrangement. Opposing sides of the aperture may diverge away from each other in a direction away from the light source.

The aperture may therefore taper towards the reflective surface upon which light from the light source impinges. A surface of a first one of the opposing sides may lie in a plane which is generally and more specifically substantially parallel to a direction travelled by light from the reflective surface towards the window. The surface of the first side may be disposed closer to the light source than a surface of the opposing, i.e. second, side. A surface of the second side may lie in a plane which is generally and more specifically substantially parallel to a direction travelled by light from the light source towards the reflective surface.

The light module may further comprise at least one optical component, such as a lens. The at least one optical component may be disposed between the light source and the beam redirection arrangement. Alternatively or in addition the light module may further comprise a light stopping arrangement, which is operative to at least reduce if not stop acquisition of a reflection which does not impinge on the imaging subject. The light stopping arrangement may comprise an opaque device which is, for example, disposed in a path between the beam redirection arrangement and the light source. Alternatively or in addition the light stopping arrangement may comprise a light absorbing arrangement which is disposed so as to absorb reflected light. For example an inside surface of the lighting module may be configured to be light absorbing, such as by being matt black. Alternatively or in addition an effect of reflected light on an acquired image may be removed or reduced by electronic processing of an acquired image.

The image acquisition apparatus may comprise a light retaining arrangement disposed so as to retain or trap light received in the aperture from the light source which passes through the beam redirection arrangement. The light retaining arrangement may therefore comprise a light trap. The light retaining arrangement may be disposed on an inside of the image acquisition apparatus opposing a side from which light is emitted by the light source.

The main body may define a first aperture which is configured to receive the lighting module. The first aperture may be defined in a side of the main body. The first aperture may be substantially circular. The main body may define a second aperture configured to receive an end of the lighting module. The first and second apertures may be coaxially disposed. The second aperture may therefore be defined in a side of the main body opposing the side defining the first aperture. The main body and the lighting module may be configured such that the lighting module is a snug fit in the first and second apertures whereby a proper optical disposition of the lighting module and the main body may be achieved. The lighting module may be elongate. The lighting module may be generally and perhaps substantially cylindrical in form.

The imaging arrangement and the main body may define cooperating profiles which provide for the releasable coupling of the imaging arrangement and the main body. The main body may define an aperture for receiving at least a part of the imaging arrangement. The main body may be configured to couple with the imaging arrangement towards an end of the main body opposite an end of the main body comprising the window. The imaging arrangement may comprise an imaging device, such as a Charge Coupled Device (CCD), which is disposed in the imaging arrangement so as to define an end of an imaging path in the portable image acquisition apparatus. The imaging arrangement may further comprise an imaging arrangement housing which supports the imaging device. The imaging arrangement may further comprise imaging processing electronics which is operative to read data acquired by the imaging device. The imaging arrangement may further comprise data storage, e.g. flash memory, which is configured such that it is operative to store at least one acquired image. The imaging arrangement may further comprise a communications arrangement which is operative to communicate acquired image data to a spaced apart location. More specifically the communications arrangement may be configured for wired communication of acquired image data, e.g. to the like of a Personal Computer (PC). The wired communication may be in accordance with at least one of USB, firewire, Ethernet, HDMI, SCSI, SATA or like protocols or standards. Alternatively or in addition the communications arrangement may be configured for wireless communication with a remote device, such as a PC. The wireless communication may be in accordance with at least one of Bluetooth, wireless Ethernet, 3G or like protocols or standards. The imaging arrangement may further comprise an orientation determining arrangement which is operative to determine an orientation of the portable image acquisition apparatus. The orientation determining arrangement may comprise at least one accelerometer, such as a three axis accelerometer. The presence of at least one accelerometer may provide for determination of whether the apparatus is being used with the left eye or the right eye.

The main body may be elongate in form. The window may be disposed towards a first end of the elongate main body. The portable image acquisition apparatus may be configured such that the imaging arrangement is disposed towards a second, opposite end of the elongate main body. When the lighting module is coupled with the main body the portable image acquisition apparatus may be configured such that the lighting module is disposed between the window and the imaging arrangement.

The main body may comprise a housing. The housing may comprise a user operable control, e.g. one or more push button switches, to actuate at least one of the lighting module and the imaging arrangement. Alternatively or in addition the housing may comprise a user operable control which provides for variation in intensity of light emitted by the light source. Variation in intensity of light emitted by the light source may be provided by varying current flowing through the light source. The user operable control may, for example, be a rotary device such as a rotary potentiometer.

The main body may comprise at least one optical device. The optical device may be operative on an image between the window and the imaging arrangement. The main body may comprise an objective lens arrangement disposed towards the window. The objective lens arrangement may comprise an objective lens pair and more specifically an achromatic lens pair. The objective lens pair may have a focal length between 15 mm and 45 mm, 20 mm and 40 mm, or 25 mm and 35 mm. More specifically the objective lens pair may have a focal length of 30 mm. The main body may comprise an imaging lens arrangement disposed towards the imaging arrangement. The imaging lens arrangement may comprise an imaging lens pair and more specifically an achromatic lens pair. The imaging lens pair may have at least one focal length between 5 mm and 35 mm, 10 mm and 30 mm, or 15 mm and 25 mm. More specifically the objective lens pair may have focal lengths of 20 mm and 25 mm.

The main body may comprise a polariser disposed in an imaging path between the window and the imaging arrangement. More specifically the polariser may be disposed between the optical arrangement and the window. Where the main body comprises an objective lens arrangement the polariser may be disposed between the objective lens arrangement and the optical arrangement. The polariser may be disposed at an angle to the direction of the imaging path between the window and the imaging arrangement. More specifically the polariser may be disposed at an angle of between 10 and 40 degrees and more specifically between 20 and 30 degrees about at least one of a first axis which is orthogonal to the direction of the imaging path and a second axis which is orthogonal to the direction of the imaging path, the first and second axes being orthogonal to each other. More specifically the polariser may be disposed at an angle of between 20 and 30 degrees about one of the first and second axes and more specifically the first axis where the first axis extends in substantially a same direction as an axis about which an angled surface of a beam splitter is angled in relation to the direction of the imaging path. Angulation of the polariser may provide for a reduction in reflection from the surface of a polarising medium comprised in the polariser which otherwise would be liable to compromise operation of the portable image acquisition apparatus.

The portable image acquisition apparatus may comprise a reflex blocker in the imaging path between the window and the imaging arrangement. More specifically the reflex blocker may be disposed between the optical arrangement and the imaging arrangement. Where the main body comprises an imaging lens arrangement the reflex blocker may be disposed between the imaging lens arrangement and the imaging arrangement.

The portable image acquisition apparatus may further comprise an interface arrangement which is configured to provide for ease of acquisition of an image from a particular shape of part of the human or animal body. The interface arrangement may be a module. The interface arrangement and the main body may define cooperating surface profiles which provide for releasable coupling of the interface arrangement to the main body. The interface arrangement may be configured to conform to a part of the human or animal body. The interface arrangement may define a particular profile, such as a profile which fits around the eye of a human or animal. An interface arrangement which is configured to conform to a part of the human or animal body may reduce the amount of background light impinging on the imaging subject. A reduction in the amount of background light impinging on the imaging subject may be beneficial such as in respect of reducing the extent to which the pupil contracts where the imaging subject is an eye. The interface arrangement may be configured to provide for a conformable profile whereby the interface arrangement may accommodate differences in shapes of parts of the human or animal body from subject to subject. The interface arrangement may, for example, comprise a pliable portion. According to another example the interface arrangement may be configured to acquire images from the skin of a subject. According to yet another example the interface arrangement may be configured by way of an otoscope interface to acquire images from the inside of an ear of a subject.

The portable image acquisition apparatus may be configured to be hand portable and more specifically configured to be held in one hand. The portable image acquisition apparatus may be configured to be held and operated with one hand. The main body may be shaped such that it and thus the portable image acquisition apparatus can be gripped in one hand. The portable image acquisition apparatus may be of a length of no more than substantially 300 mm, 250 mm, 200 mm, 175 mm, 150 mm, 125 mm, 110 mm or 100 mm. In a form the portable image acquisition apparatus may be of a length of 157 mm. The portable image acquisition apparatus may be of a width of no more than substantially 175 mm, 150 mm, 125 mm, 110 mm, 100 mm, 90 mm, 80 mm or 70 mm. In a form the portable image acquisition apparatus may be generally rectangular in cross section with the cross section having dimensions of 57 mm by 87 mm. The portable image acquisition apparatus may be of a weight of no more than substantially 2 kg, 1.5 kg, 1.25 kg, 1 kg, 0.75 kg, 0.5 kg, 0.25 kg, 0.2 kg, 0.15 kg or 0.1 kg. In a form the portable image acquisition apparatus may weigh about 0.250 kg. The portable image acquisition apparatus may be configured such that the imaging path within the portable image acquisition apparatus consists of one linear path. The portable image acquisition apparatus may be configured such that the light beam within the portable image acquisition apparatus follows no more than a first linear path followed by a second linear path, the first and second linear paths extending in different directions and more specifically orthogonal directions.

The portable image acquisition apparatus may be configured such that a working distance between the objective end of the portable image acquisition apparatus and the subject being imaged is greater than 5 mm, 10 mm, 15 mm or 20 mm. The portable image acquisition apparatus may be configured such that a working distance is no greater than 50 mm, 40 mm, 30 mm, 25 mm, 20 mm, 15 mm or 10 mm.

The portable image acquisition apparatus may be configured for battery powered operation. The imaging arrangement may therefore comprise a battery holder arrangement configured to hold at least one battery and to provide for drawing of electrical power therefrom for operation of at least one of the lighting module and the imaging arrangement. Alternatively or in addition the portable image acquisition apparatus may be configured to receive electrical power from an external source of power, such as by way of a wired link between the portable image acquisition apparatus and other apparatus, such as a PC.

According to a second aspect of the present invention there is provided a method of acquiring at least one image of a part of a human or animal body by way of portable image acquisition apparatus according to the first aspect of the present invention. The method may comprise disposing the window defined by the main body of the portable image acquisition apparatus relative a part of a human or animal body to be imaged. The method may further comprise operating the portable image acquisition apparatus such that the beam of light impinges on the part of the human or animal body to be imaged and at least one image of the part of the human or animal body is acquired by the imaging arrangement.

As described above the portable image acquisition apparatus may comprise an interface arrangement which is configured to provide for ease of acquisition of an image from a particular shape of part of the human or animal body. Although the present invention is described herein with reference to the acquisition of images of the eye and more specifically the retina or anterior portion of the eye, the apparatus may be configured to acquire images from other parts of human and animal subjects. The method may therefore comprise acquiring at least one image of: skin of a human or animal; hair of a human or animal; a toenail, a fingernail, a hoof or the like of a human or animal; and an inside view of a human or animal, such as of a nostril, ear, mouth, vagina or rectum.

Further embodiments of the second aspect of the present invention may comprise one or more features of the first aspect of the present invention.

The present inventor has appreciated the second embodiment of the beam redirection arrangement to be of wider applicability than hitherto described. According to a third aspect of the present invention there is therefore provided an optical arrangement comprising a beam redirection arrangement, a light source and a window through which light is emitted from the optical arrangement, the beam redirection arrangement comprising a substantially completely reflective surface and defining an aperture, the optical arrangement being configured such that the light source and the beam redirection arrangement are disposed relative each other whereby light emitted by the light source impinges on the aperture and the reflective surface, the light impinging on the aperture being substantially completely transmitted through the beam redirection arrangement and the light impinging on the reflective surface being reflected towards the window.

The beam redirection arrangement of the present aspect is operative in the same fashion as the beam redirection arrangement of the first aspect as described above. In common with the beam redirection arrangement of the first aspect the aperture of the beam redirection arrangement of the present aspect may be disposed in the beam redirection arrangement so as to leave an imaging path between the window and an imaging end of the optical apparatus substantially unimpeded whereby an image passes substantially through the aperture towards the imaging end. In view of the reflective surface being disposed at an angle to the light source whereby light is redirected towards the window, opposing sides of the aperture may diverge away from each other to thereby minimise reflection of light received from the light source from the opposing sides and to provide for passage of the image towards the imaging end. Opposing sides of the aperture may diverge away from each other in a direction away from the light source. The aperture may therefore taper towards the reflective surface upon which light from the light source impinges. Further embodiments of the present aspect of the invention may comprise one or more features of the first aspect of the present invention.

According to a further aspect of the present invention there is provided image acquisition apparatus configured to acquire at least one image of a part of a human or animal body, the apparatus comprising: a main body defining a window; a lighting arrangement operative to direct a beam of light through the window; and an imaging arrangement operable to acquire an image of the part of the human or animal body by way of an imaging path passing through the window. Embodiments of the further aspect of the present invention may comprise one or more features of any previous aspect of the present invention.

BRIEF DESCRIPTION OF DRAWINGS

The present invention will now be described by way of example only with reference to the following drawings, of which.

DESCRIPTION OF EMBODIMENTS

Figure 1A:
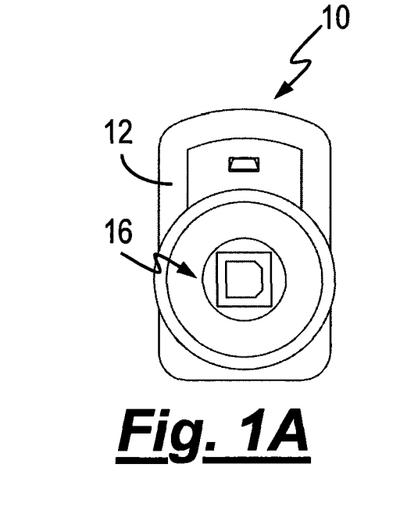
FIG. 1A is an end view of an embodiment of the present invention looking towards the back of the imaging arrangement.
Figure 1B:
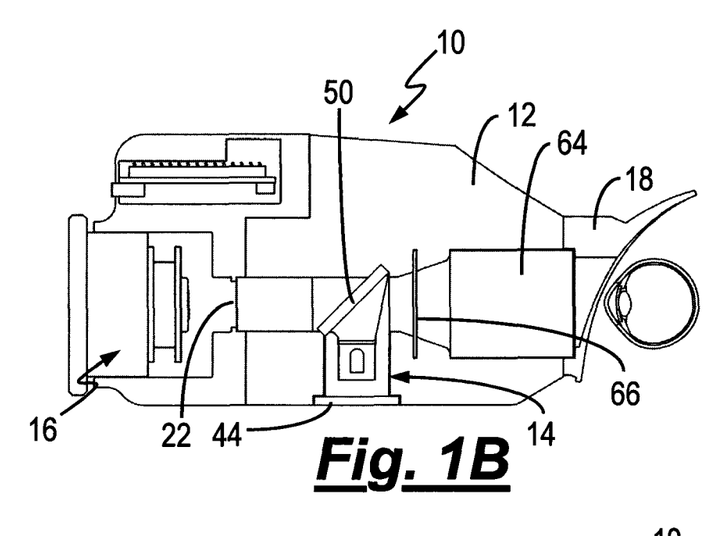
FIG. 1B is a side view in section of the embodiment of FIG. 1A.
Figure 1C:
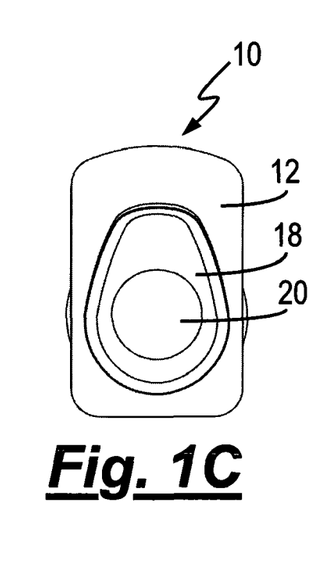
FIG. 1C is an end view of the embodiment of FIG. 1A looking towards the window at the objective end.
Figure 1D:
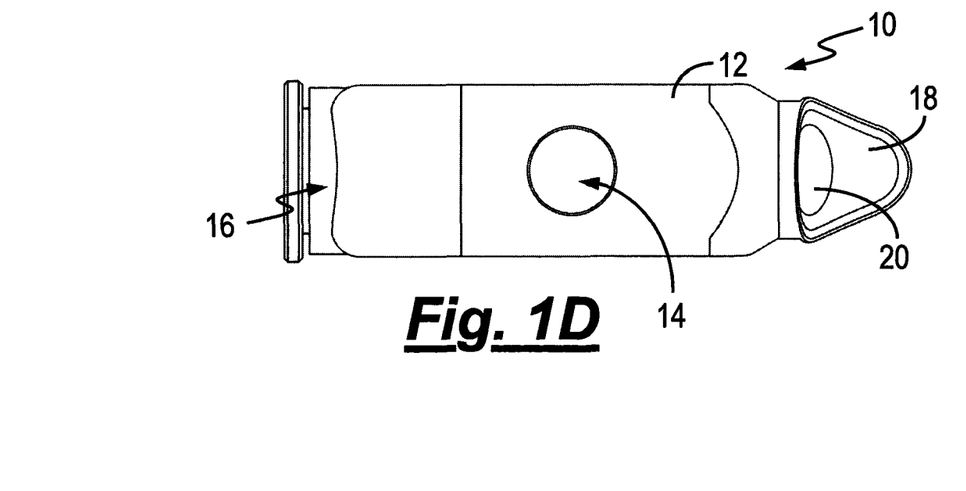
FIG. 1D is a side view of the embodiment of FIG. 1A when the embodiment has been rotated through ninety degrees from the position shown in FIG. 1B.

Portable image acquisition apparatus 10 according to an embodiment of the present invention is shown in FIGS. 1A to 1D. FIG. 1A shows an end view of the embodiment towards the back of the imaging arrangement. FIG. 1B shows a side view in section of the embodiment. FIG. 1C shows an end view of the embodiment looking towards the window at the objective end. FIG. 1D shows a side view of the embodiment when the embodiment has been rotated through ninety degrees from the position shown in FIG. 1B.

Components of the embodiment of portable image acquisition apparatus 10 will now be described with reference to FIGS. 1A to 1D. The portable image acquisition apparatus 10 comprises a housing 12 which is elongate in form and generally rectangular in cross section. The portable image acquisition apparatus 10 further comprises a lighting module 14, which is removably received in apertures defined by the housing 12, and an imaging arrangement 16, which removably couples with a distal end of the housing (i.e. an end of the housing furthest away from the part of the human or animal body to be imaged). The portable image acquisition apparatus 10 yet further comprises an interface arrangement 18 which is removably coupled to the proximal end of the housing (i.e. an end of the housing nearest the part of the human or animal body to be imaged). The portable image acquisition apparatus 10 is substantially 157 mm long (including the interface arrangement) and weighs substantially 0.229 kg. As can be seen from FIGS. 1A and 1C the portable image acquisition apparatus is generally rectangular in cross section. The portable image acquisition apparatus has a width of 57 mm and a height of 87 mm. As can be seen from FIGS. 1C and 1D the proximal end of the housing 12 defines a window 20 through which a subject may be imaged. Although not shown in detail in FIGS. 1A to 1D but shown in detail in FIG. 3 an objective lens arrangement 64 is provided near the window to manipulate at least one of a light beam generated by the lighting module 14 and passing through the window 20 and an image acquired by the imaging arrangement 16 by way of the window 20. As can be seen from FIG. 1B an aperture 22 is defined within the housing 12. The housing defined aperture 22 enables an imaging device (not shown) of the imaging arrangement 16 to see an image of the subject as composed by the optics comprised in the portable image acquisition apparatus 10.

The housing 12 of the portable image acquisition apparatus 10 and housings of the lighting module 14 and the imaging arrangement 16 are formed from a plastics material such as ABS. As mentioned above the portable image acquisition apparatus 10 is configured such that each of the lighting module 14, the imaging arrangement 16 and the interface arrangement 18 are removably coupled with the housing 12. The housing 12 further comprises a push button switch which is not evident in FIGS. 1A to 1D and which is user operable to actuate the lighting module and the imaging arrangement when the user wishes to acquire at least one image of a subject. The push button switch is disposed on the housing such that the user can grip the housing 12 and operate the push button switch with one hand. The parts of the portable image acquisition apparatus 10, their interengagement and their operation are described further below.

Figure 2:
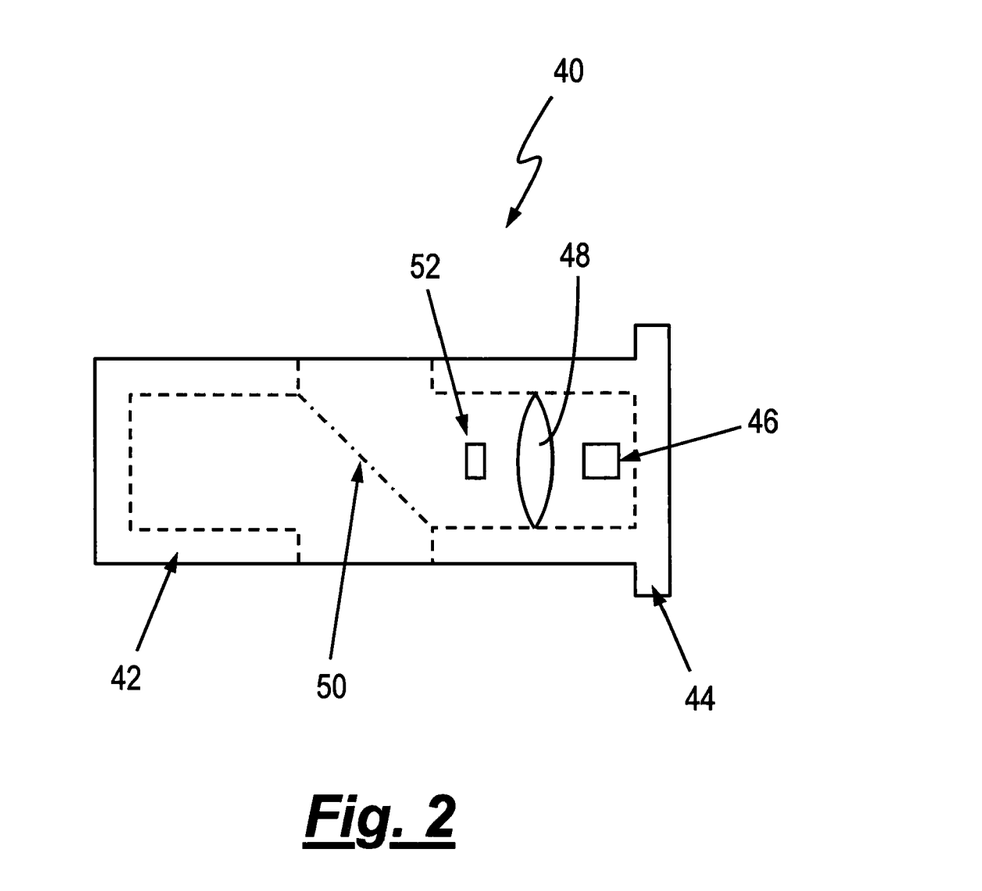
FIG. 2 is a sectional view through the lighting module of the embodiment of FIG. 1A.

A representation of a sectional view through the lighting module 14 of the embodiment of FIG. 1A is shown in FIG. 2. Although the dimensions and relative disposition of the components of the lighting module 40 of FIG. 2 differ from the components of the lighting module 14 as shown in FIG. 1B their form and function are the same. The lighting module 40 of FIG. 2 comprises a lighting housing 42 with the internal features of the housing 42 being indicated in FIG. 2 by way of dashed lines. The lighting housing 42 is generally tubular in form and defines an end cap 44 which extends beyond the main body of the lighting module. Opposing sides of the main body of the lighting module 40 define first and second apertures which are in registration with each other so as not to obstruct the imaging path. The end cap 44 is received in a stepped recess defined around an aperture in the side of the housing 12 of the portable image acquisition apparatus 10 when the main body of the lighting module 14, 40 is received through the aperture in the side of the housing 12. The lighting module 40 comprises a light source 46, a lens 48 and a beam splitter 50 which is described further below. The light source 46 comprises plural LEDs which are operative to selectively emit broadband visible light, infrared light or green light. The light source 46 is operative to emit light of an intensity of 2 candelas. The light source 46 emits a beam of light through the lens 48 such that the beam of light impinges on the beam splitter 50 which is operative to reflect most of the light beam such that a direction of the light beam is changed through 90 degrees. As can be seen appreciated from FIG. 1B, the beam splitter 50 redirects the light beam such that it is directed towards the window 20 formed by the housing 12 such that it impinges on the imaging subject. Redirection of the light beam causes the redirected part of the light beam to be substantially coaxial with an imaging path between the window 20 and the imaging device of the imaging arrangement 16. In view of the beam splitter 50 being located in the imaging path between the window and the imaging device the beam splitter 50 is configured for visibility of the imaging subject through the beam splitter 50 as is described further below. The lighting module 40 further comprises a reflex block 52 (which constitutes a light stopping arrangement) which is disposed between the lens 48 and the beam splitter 50 and which is operative to at least reduce if not stop acquisition of a reflection other than a reflection of the imaging subject. Other means of reflection blocking are employed, such as polarising the light beam and coating inside surfaces of the image acquisition apparatus with light absorbing material.

The imaging arrangement 16 of FIGS. 1A to 1D comprises a housing which contains and supports a battery and a battery housing arrangement, flash memory (which constitutes data storage) and an accelerometer (which constitutes an orientation determining arrangement). The imaging arrangement 16 further comprises a CCD device (which constitutes an imaging device), a wired transmitter which is operative to drive signals down a copper or optical lead, and a wireless transceiver. The housing of the imaging arrangement 16 is shaped to releasably couple with the housing 12 of the portable image acquisition apparatus 10. Upon operation of the CCD device images are acquired and stored in the flash memory. Stored image data is then conveyed away from the portable image acquisition apparatus 10 for analysis elsewhere by way of a wired communications channel provided in part by the wired transmitter or by way of a wireless communications channel provided in part by the wireless transceiver. The wireless transceiver is in addition used to configure the portable image acquisition apparatus, e.g. by way of a Personal Computer.

The interface arrangement 18 of the portable image acquisition apparatus is configured to conform to an eye socket is shown in FIG. 1B. A proximal end of the interface arrangement 18 defines a stepped profile at its outer periphery which provides for releasable coupling with a corresponding stepped profile defined in the proximal end of the housing 12. A main body of the interface arrangement 18 is shaped to fit over an eye socket of a human or animal subject. The main body is formed of pliable biocompatible material, such as medical grade silicone rubber, whereby the main body is capable of conforming to eye sockets of different shapes to thereby shield the eye from extraneous light.

Figure 3:
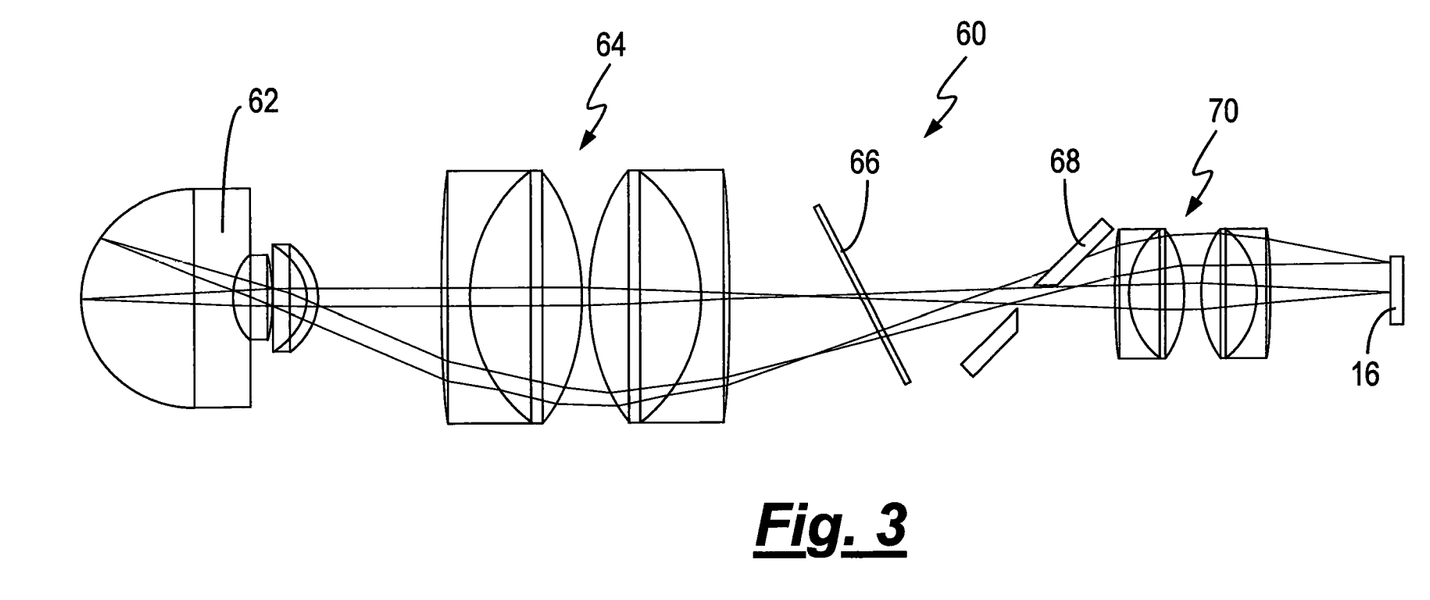
FIG. 3 shows the optical components of the embodiment of FIG. 1A.

The optical arrangement 60 of the portable image acquisition apparatus 10 is shown in FIG. 3. The eyeball 62 is represented by the graphic shown in FIG. 3 at the objective end of the optical arrangement. The optical arrangement 60 comprises an objective lens pair 64 having a focal length of 30 mm. The objective lens pair is a 30 mm achromatic pair 1:1 with 30 mm and 30 mm EFL achromats from Edmunds Optics Limited of Unit 1, Opus Avenue, Nether Poppleton, York, YO26 6BL, UK. Of the optical components of the optical arrangement 60, the objective lens pair 64 is disposed closest to the eye being imaged. The optical arrangement 60 also comprises a circular polariser 66 which is disposed on the imaging side of the objective lens pair 64. Although the circular polariser 66 is not angled in the embodiment of FIG. 1B, in the embodiment of FIG. 3 the circular polariser 66 is disposed at an angle of between 20 and 30 degrees about an axis which extends in substantially a same direction as an axis about which the angled surface of the beam splitter 50 of FIG. 1B is angled in relation to the direction of the imaging path. The optical arrangement 60 further comprises a beam splitter 68 which is disposed on the imaging side of the polariser 66. The beam splitter 68 is described further below. The optical arrangement 60 yet further comprises an imaging lens pair 70 which is disposed on the imaging side of the beam splitter 68 and on the objective side of the imaging arrangement 16. The imaging lens pair 70 is a 15 mm achromatic pair 1:1.25 with 20 mm and 25 mm EFL achromats from Edmunds Optics Limited. In another un-illustrated embodiment in which monochromatic light is emitted from the light source the objective lens and imaging lens pairs are non-achromatic. The polariser 66 is operative to reduce light reflex which would otherwise cause a bright spot on the acquired image. The polariser 66 is operative to circularly polarise light reflected by the beam splitter 68 towards the window. Whatever proportion of the light is reflected by the objective lens pair 64 maintains polarisation and is rejected by the polariser 66 in view it travelling in the opposite direction whereby light reflex is obviated. On the other hand light from the imaging subject does not preserve polarisation and therefore passes through the polariser 66.

The optical arrangement 60 is configured such that the working distance between the objective end of the portable image acquisition apparatus 10 and the subject, e.g. eye, being imaged is between 10 mm and 20 mm.

Figure 4A:
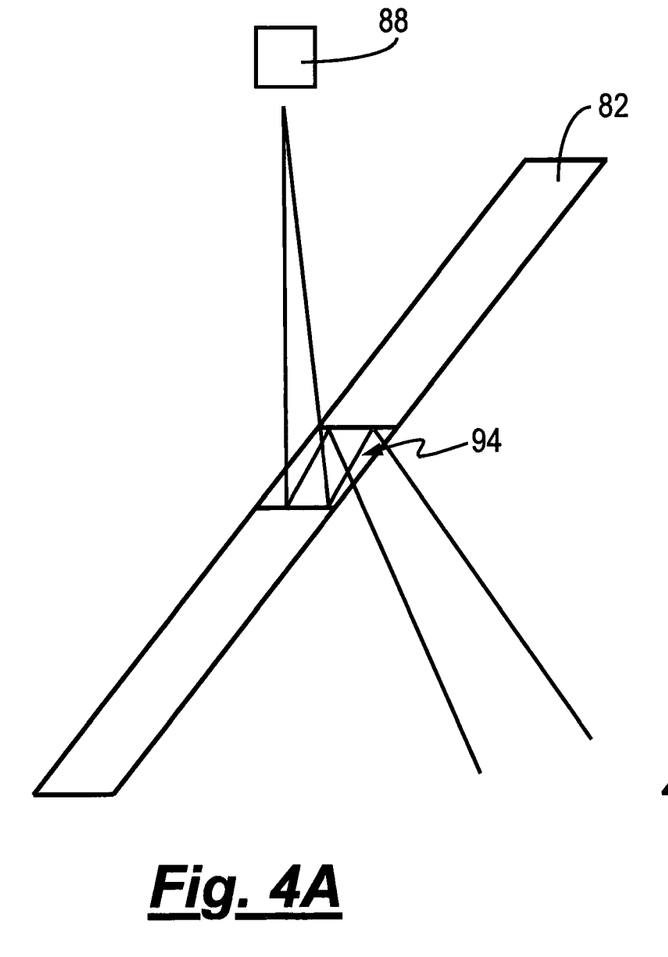
FIG. 4B shows the beam splitter of the present embodiment and FIG. 4A shows an alternative form of beam splitter.
Figure 4B:
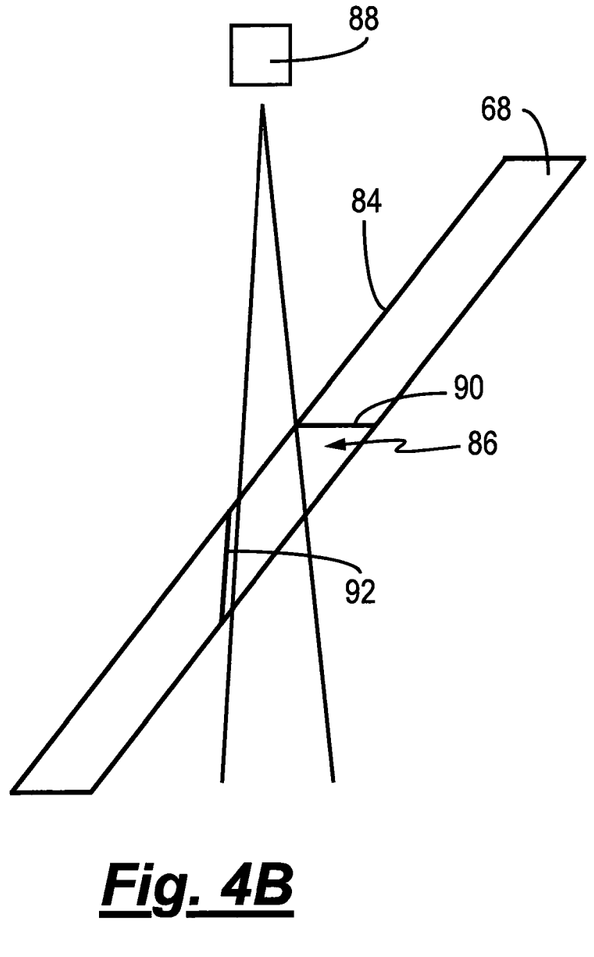

FIG. 4B shows the beam splitter 68 of the present embodiment and FIG. 4A shows an alternative form of beam splitter 82. The beam splitter 68 of FIG. 4B comprises a substantially completely reflective surface 84 and defines a centrally disposed aperture 86 which provides for substantially complete transmission of light from the light source 88 which impinges on the aperture. Light not impinging on the aperture, i.e. light impinging on the reflective surface 84 is reflected towards the window 20. In addition the aperture 86 is shaped so as to leave the imaging path substantially unimpeded whereby the image passes substantially through the aperture towards the imaging arrangement. As can be seen from FIG. 4B opposing sides of the aperture 86 diverge away from each other in a direction away from the light source 88. A surface of a first one 90 of the opposing sides lies in a plane which is substantially parallel to a direction travelled by light from the reflective surface 84 towards the window 20. The surface of the first side 90 is disposed closer to the light source 88 than a surface of the opposing, i.e. second, side 92. A surface of the second side 92 lies in a plane which is substantially parallel to a direction travelled by light from the light source 88 towards the reflective surface 84. The structure and formation of the aperture is described further below with reference to FIGS. 5A to 5C. The alternative form of beam splitter 82 shown in FIG. 4A has an aperture 94 defined by opposing surfaces which are parallel to each other. As can be seen from FIG. 4A the opposing surfaces of the aperture 94 are operative to reflect the light from the light source 88 and thereby decrease efficiency. In a less preferred and un-illustrated form the beam splitter 68 comprises either a surface which at any location is partially reflective and partially transmissive or is constituted by a dichroic device.

Figure 5A:
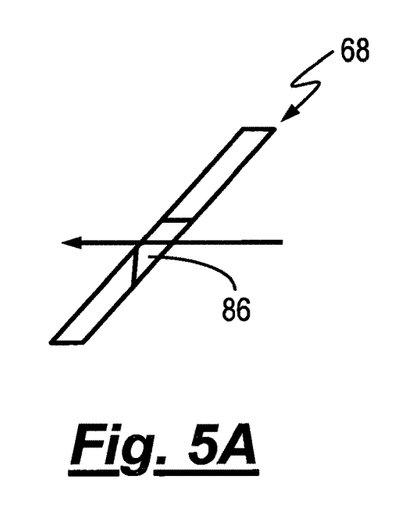
FIGS. 5A to 5C show views of the beam splitter from three different sides.
Figure 5B:
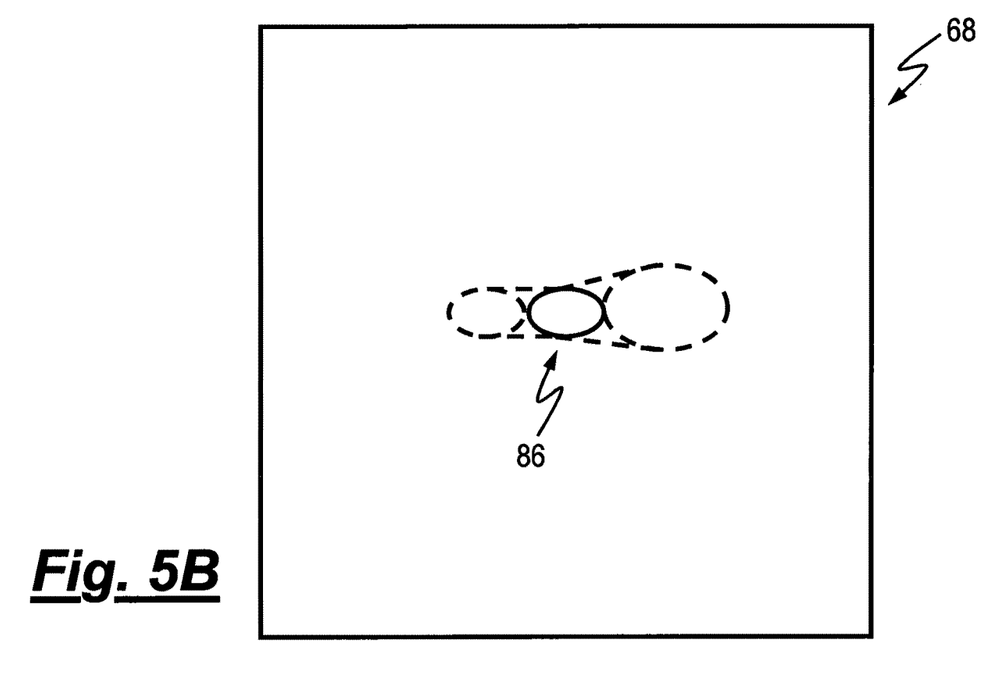
Figure 5C:
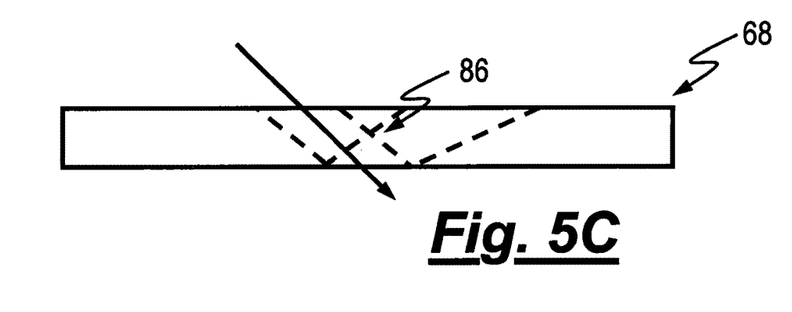

FIGS. 5A to 5C show views of the beam splitter 68 from three different sides. FIG. 5A shows the beam splitter 68 from above with the arrow indicating the line of sight from the imaging arrangement. FIG. 5B shows the beam splitter 68 from the front. FIG. 5C shows the beam splitter 68 from the side with the arrow indicating the line of sight from the imaging arrangement. The aperture 86 is formed by drilling a first bore of diameter 3 mm in a thin mirror and then boring a second bore of the same diameter at ninety degrees to the first bore.

In other forms of the invention the interface arrangement 18 of FIGS. 1A to 1D is replaced with an alternative interface arrangement which is configured to providing for imaging of a part of a human or animal body other than the eye. In one form the alternative interface arrangement comprises an otoscope interface for imaging of the inside of the ear. The optical components comprised within the portable image acquisition apparatus 10 are changed where it is necessary to provide optical characteristics appropriate for otoscopic imaging. In another form the alternative interface arrangement comprises a main body shaped to conform to a portion of skin of a human or animal subject.

The invention claimed is:

1. Portable image acquisition apparatus configured to acquire at least one image of a part of a human or animal body, the apparatus comprising:
a main body defining a window;
an imaging arrangement operable to acquire an image of a part of a human or animal body by way of an imaging path which passes through the window; and
a lighting module comprising a light source and an optical arrangement, wherein the optical arrangement comprises a beam redirection arrangement, the lighting module being substantially contained in the main body, the lighting module and the main body being configured to detachably couple with each other when in use,
wherein the light source is configured to emit a beam of non-coherent light in a direction substantially perpendicular to the imaging path to the beam redirection arrangement,
wherein the beam redirection arrangement comprises a substantially completely reflective surface and defines an aperture in the reflective surface, the reflective surface reflecting a part of the beam of non-coherent light received from the light source and impinging on the reflective surface to direct the reflected part of the beam of non-coherent light through the window and thereby change a direction of propagation of the part of the beam of non-coherent light, and the aperture leaving the imaging path substantially unimpeded whereby the image passes substantially through the aperture towards the imaging arrangement, the portable image acquisition apparatus being configured such that between the beam redirection arrangement and the window the imaging path and the reflected part of the beam of non-coherent light are substantially coaxial, have substantially opposite directions and at least in part occupy the same space,
wherein the imaging arrangement is operative to acquire the image of the part of a human or animal body through the window and the aperture of the beam redirection arrangement as the reflected part of the beam of non-coherent light is directed through the window by the reflective surface of the beam redirection arrangement.

2. Portable image acquisition apparatus according to claim 1 configured such that the imaging path between the window and the imaging arrangement is substantially straight.

3. Portable image acquisition apparatus according to claim 1 in which the main body and the imaging arrangement are configured to detachably couple with each other when in use.

4. Portable image acquisition apparatus according to claim 3 configured such that the lighting module and the imaging arrangement are detachably coupled independently of each other to the main body.

5. Portable image acquisition apparatus according to claim 1 in which the light source is configured to emit light of an intensity of no more than 5 candelas.

6. Portable image acquisition apparatus according to claim 1 in which the optical arrangement is operative as a beam splitter.

7. Portable image acquisition apparatus according to claim 1 in which the aperture provides for substantially complete transmission through the beam redirection arrangement of another part of the beam of non-coherent light which falls over the aperture.

8. Portable image acquisition apparatus according to claim 1 in which opposing sides of the aperture diverge away from each other in a direction away from the light source to thereby minimize reflection of light from the opposing sides and to allow for passage of the image towards the imaging arrangement.

9. Portable image acquisition apparatus according to claim 1 in which the main body is elongate in form, the window is disposed towards a first end of the elongate main body and the imaging arrangement is disposed towards a second, opposite end of the elongate main body.

10. Portable image acquisition apparatus according to claim 9 in which the main body comprises an objective lens arrangement disposed towards the window and an imaging lens arrangement disposed towards the imaging arrangement.

11. Portable image acquisition apparatus according to claim 1 in which the main body comprises a polarizer disposed in an imaging path between the window and the imaging arrangement.

12. Portable image acquisition apparatus according to claim 1 further comprising an interface arrangement which is configured to conform to a part of the human or animal body.

13. Portable image acquisition apparatus according to claim 1 in which the light source comprises at least one Light Emitting Diode (LED).

14. Portable image acquisition apparatus according to claim 1 configured to acquire at least one image from an eye of a human or animal subject.

15. Portable image acquisition apparatus according to claim 1 configured to be simultaneously held with and operated manually by one hand.

16. Portable image acquisition apparatus according to claim 1, wherein the imaging path of the image acquired by the imaging arrangement passes in a direction through the window toward the imaging arrangement, and wherein the reflected part of the beam of non-coherent light is directed through the window away from the main body.

17. Portable image acquisition apparatus according to claim 1, wherein the lighting module is removably received in an aperture defined by the main body so that the lighting module and the main body are configured to detachably couple with each other when in use.

18. Portable image acquisition apparatus according to claim 1, wherein the optical arrangement is in the imaging path between the window and the imaging arrangement, and the optical arrangement is configured for transmission of the image with substantially no change in a direction of the imaging path between the window and the imaging arrangement.

19. Portable image acquisition apparatus according to claim 1, wherein the imaging path between the window and the imaging arrangement consists of one linear path and the beam of light between the light source and the window propagates along no more than a first linear path and a second linear path, the first and second linear paths extending in substantially orthogonal directions.

20. Portable image acquisition apparatus according to claim 1, wherein the imaging path and the reflected part of the beam of non-coherent light overlap in a plane of the part of the human or animal body being imaged.

21. Portable image acquisition apparatus according to claim 1, wherein the beam redirection arrangement is stationary when the lighting module is contained in the main body such that while the imaging arrangement acquires the image there is substantially no change in angle between: (a) the beam of non-coherent light between the light source and the beam redirection arrangement; and (b) the reflected part of the beam of non-coherent light between the beam redirection arrangement and the window.

22. Portable image acquisition apparatus according to claim 12, wherein the interface arrangement conforms to an eye socket to thereby reduce background light impinging on the eye.

23. Portable image acquisition apparatus according to claim 21, wherein the interface arrangement comprises a pliable portion whereby the interface arrangement conforms to differently shaped eye socket.

* * * * *